(12) United States Patent
Bamford

(10) Patent No.: US 7,827,981 B2
(45) Date of Patent: Nov. 9, 2010

(54) METHOD FOR REDUCING THE WORK OF BREATHING

(75) Inventor: Owen S. Bamford, Linthieum Heights, MD (US)

(73) Assignee: Vapotherm, Inc., Stevensville, MD (US)

( * ) Notice: Subject to any disclaimer, the term of this patent is extended or adjusted under 35 U.S.C. 154(b) by 68 days.

(21) Appl. No.: 10/833,843

(22) Filed: Apr. 27, 2004

(65) Prior Publication Data

US 2004/0200476 A1 Oct. 14, 2004

Related U.S. Application Data

(63) Continuation-in-part of application No. 10/149,356, filed on Jan. 29, 2003.

(51) Int. Cl.
*A61M 11/00* (2006.01)
(52) U.S. Cl. .............. 128/200.14; 128/203.17; 128/203.26
(58) Field of Classification Search ........... 128/200.24, 128/203.17, 203.27, 203.26, 204.17, 204.18, 128/204.21, 204.23
See application file for complete search history.

(56) References Cited

U.S. PATENT DOCUMENTS

| | | | |
|---|---|---|---|
| 3,491,754 A | 1/1970 | Weese | |
| 3,616,796 A | 11/1971 | Jackson | |
| 3,638,926 A * | 2/1972 | Melville et al. | 261/130 |
| 3,864,440 A | 2/1975 | Giocoechea | |
| 3,871,373 A | 3/1975 | Jackson | |
| 3,912,795 A | 10/1975 | Jackson | |
| 3,923,057 A | 12/1975 | Chalon | |
| 3,944,635 A | 3/1976 | Siegenthaler | |
| 4,026,285 A | 5/1977 | Jackson | |
| 4,110,419 A | 8/1978 | Miller | |
| 4,134,940 A | 1/1979 | Sherman | |
| 4,137,940 A | 2/1979 | Faisandier | |
| 4,201,204 A | 5/1980 | Rinne et al. | |
| 4,204,535 A | 5/1980 | Pohlmann | |
| 4,232,667 A | 11/1980 | Chalon et al. | |
| 4,249,527 A | 2/1981 | Ko et al. | |
| 4,324,238 A | 4/1982 | Genese et al. | |
| 4,328,793 A | 5/1982 | Martin | |

(Continued)

FOREIGN PATENT DOCUMENTS

EP 0 009 543 A1 4/1980

(Continued)

OTHER PUBLICATIONS

Abstract—Effect of Vapotherm[R], A High-Flow Humidified $O^2$ Delivery Device, on Breathing in COPD Patterns During Exercise, Nugent T. Vance, G. Criner GJ, Chatlia W. Div Pulm & Crit Care, Temple School of Medicine, Pa, (Reprinted from American Journal of Respiratory and Critical Care Medicine vol. 165, No. 8, Part 2, Apr. 2002, p. A592.

(Continued)

*Primary Examiner*—Steven O Douglas
(74) *Attorney, Agent, or Firm*—RatnerPrestia

(57) ABSTRACT

The present invention relates to a method for reducing the work of breathing. Heated and humidified air is delivered through a nasal cannula to the nasal passageway of a patient at a flow rate above 20 liters/min thereby reducing inspiratory work.

10 Claims, 4 Drawing Sheets

U.S. PATENT DOCUMENTS

| | | | |
|---|---|---|---|
| 4,338,267 A | 7/1982 | Riuli et al. | |
| 4,350,647 A | 9/1982 | de la Cruz | |
| 4,372,306 A | 2/1983 | Genese et al. | |
| 4,381,267 A | 4/1983 | Jackson | |
| 4,401,114 A | 8/1983 | Lwoff et al. | |
| 4,463,755 A | 8/1984 | Suzuki | |
| 4,481,944 A | 11/1984 | Bunnell | |
| 4,495,944 A * | 1/1985 | Brisson et al. | 600/538 |
| 4,527,557 A * | 7/1985 | DeVries et al. | 128/204.23 |
| 4,621,633 A * | 11/1986 | Bowles et al. | 128/203.17 |
| 4,632,677 A | 12/1986 | Blackmer | |
| 4,682,010 A | 7/1987 | Drapeau et al. | |
| 4,686,354 A | 8/1987 | Makin | |
| 4,708,831 A | 11/1987 | Elsworth et al. | |
| 4,722,334 A | 2/1988 | Blackmer et al. | |
| 4,773,410 A | 9/1988 | Blackmer et al. | |
| 4,801,385 A | 1/1989 | Sachtler et al. | |
| 4,829,998 A | 5/1989 | Jackson | |
| 4,886,055 A | 12/1989 | Hoppough | |
| 4,911,157 A | 3/1990 | Miller | |
| 4,953,546 A | 9/1990 | Blackmer et al. | |
| 4,955,372 A | 9/1990 | Blackmer et al. | |
| 4,967,744 A | 11/1990 | Chua | |
| 5,062,145 A | 10/1991 | Zwaan et al. | |
| 5,063,994 A | 11/1991 | Verkaart | |
| 5,097,898 A | 3/1992 | Verkaart | |
| 5,101,820 A | 4/1992 | Christopher | |
| 5,218,833 A | 6/1993 | Newbold | |
| 5,236,586 A | 8/1993 | Antoni et al. | |
| 5,255,674 A | 10/1993 | Oftedal et al. | |
| 5,279,288 A | 1/1994 | Christopher | |
| 5,348,691 A | 9/1994 | McElroy et al. | |
| 5,349,946 A * | 9/1994 | McComb | 128/203.17 |
| 5,394,867 A * | 3/1995 | Swann | 128/201.25 |
| 5,396,884 A | 3/1995 | Bagwell et al. | |
| 5,617,847 A * | 4/1997 | Howe | 128/204.23 |
| 5,738,808 A | 4/1998 | Iwamoto | |
| 5,769,071 A | 6/1998 | Turnbull | |
| 5,868,133 A * | 2/1999 | DeVries et al. | 128/204.21 |
| 5,890,490 A | 4/1999 | Aylsworth et al. | |
| 6,050,260 A | 4/2000 | Daniell et al. | |
| 6,095,505 A | 8/2000 | Miller | |
| 6,102,037 A * | 8/2000 | Koch | 128/203.26 |
| 6,332,462 B1 | 12/2001 | Krohn | |
| 6,367,472 B1 | 4/2002 | Koch | |
| 6,457,472 B1 * | 10/2002 | Schwartz et al. | 128/204.23 |
| 6,516,801 B2 * | 2/2003 | Boussignac | 128/204.24 |
| 6,526,970 B2 * | 3/2003 | DeVries et al. | 128/204.21 |
| 6,653,012 B2 | 11/2003 | Suzuki et al. | |
| 6,739,338 B2 | 5/2004 | Tanhehco et al. | |
| 6,786,475 B2 | 9/2004 | Salter et al. | |
| 6,877,510 B2 | 4/2005 | Nitta | |
| 6,904,911 B2 | 6/2005 | Gibertoni | |
| 6,976,489 B2 | 12/2005 | Mantell et al. | |
| 6,988,497 B2 | 1/2006 | Levine | |
| 7,314,046 B2 * | 1/2008 | Schroeder et al. | 128/200.14 |
| 2002/0195104 A1 | 12/2002 | Fini et al. | |
| 2003/0209246 A1 | 11/2003 | Schroeder et al. | |
| 2004/0016428 A9 * | 1/2004 | Lurie | 128/202.28 |
| 2004/0221844 A1 * | 11/2004 | Hunt et al. | 128/204.17 |
| 2005/0121038 A1 * | 6/2005 | Christopher | 128/207.18 |
| 2005/0178383 A1 * | 8/2005 | Mackie et al. | 128/203.16 |
| 2007/0175473 A1 | 8/2007 | Lewis et al. | |

FOREIGN PATENT DOCUMENTS

| | | |
|---|---|---|
| EP | 0 062 913 A1 | 10/1982 |
| EP | 0 359 531 A2 | 3/1990 |
| FR | 2 164 873 | 8/1973 |
| FR | 2 311 558 | 12/1976 |
| WO | WO 86/02276 | 4/1986 |

OTHER PUBLICATIONS

International Search Report for PCT/US05/09556, search date Jul. 6, 2005.

* cited by examiner

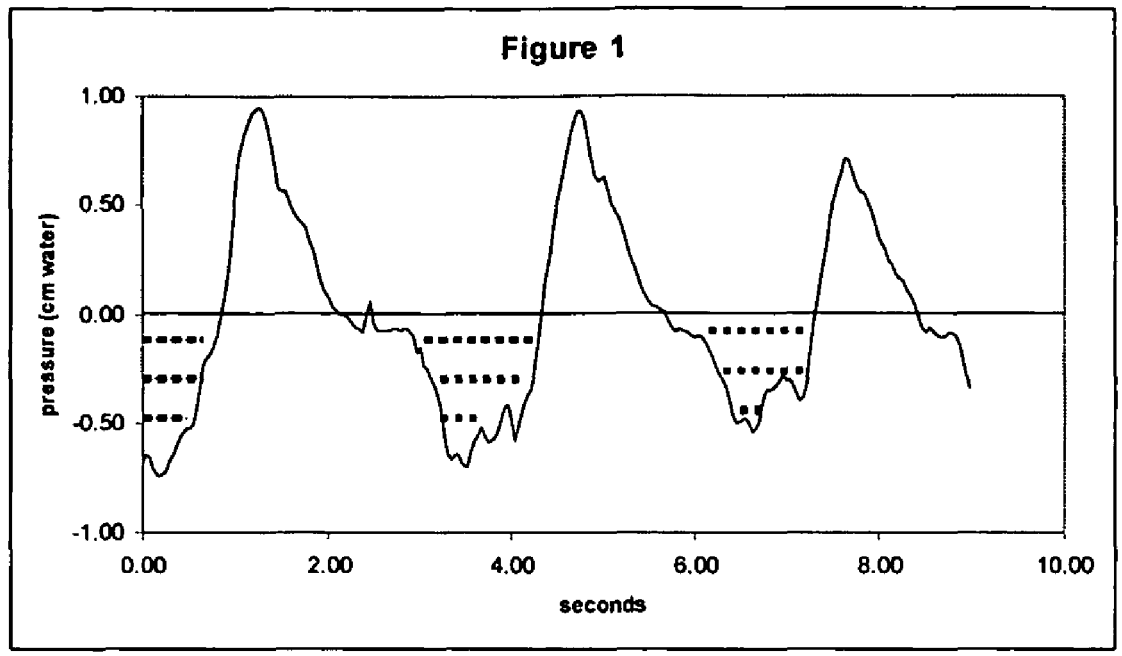
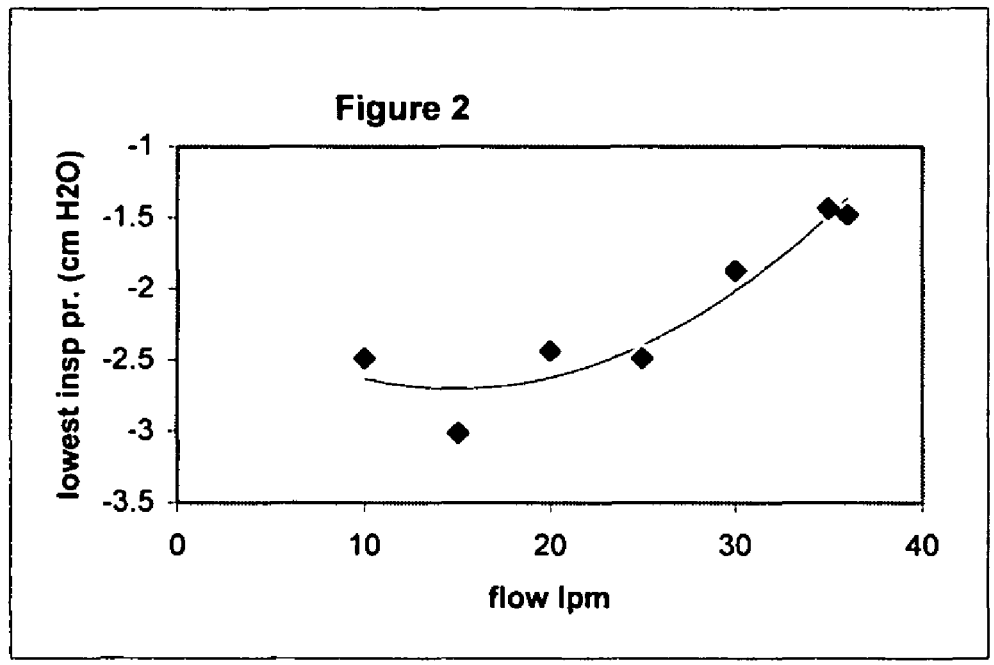

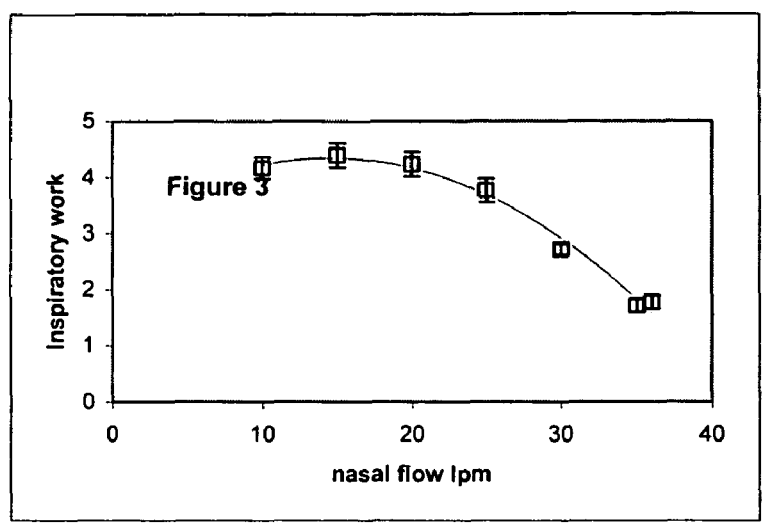
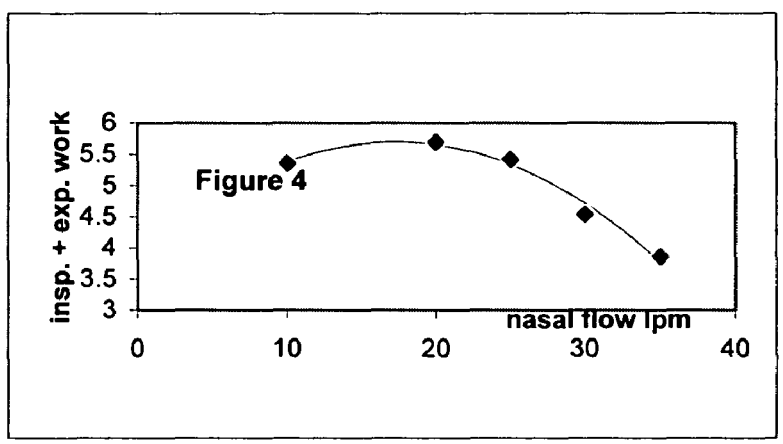
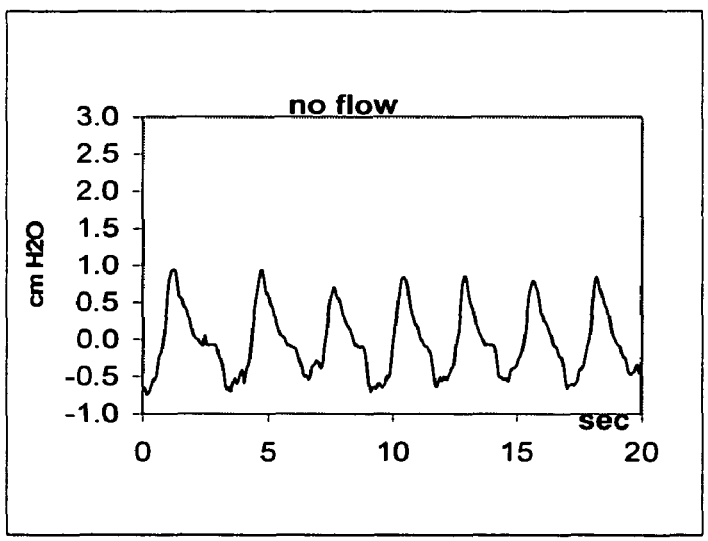
FIG. 5

METHOD FOR REDUCING THE WORK OF BREATHING

This application is a continuation-in-part of application Ser. No. 10/149,356, filed Jan. 29, 2003 (now pending), which is incorporated herein in its entirety, which is a National Stage application of PCT Application US00/33346, filed on Dec. 8, 2000, which claims priority from U.S. Provisional Patent Application Ser. No. 60/170,213, filed on Dec. 10, 1999.

FIELD OF THE INVENTION

This invention relates to the reduction of work of breathing. More particularly, this invention provides a method for reducing the work of breathing by delivering heated and humidified air to the nasal passageway of a patient.

BACKGROUND OF THE INVENTION

Breathing muscles of patients with conditions such as obstructive lung diseases must work unusually hard to overcome an increased resistance to airflow often associated with such conditions. This increased work of breathing (WOB) often causes the patient to feel short of breath, and can be so severe in some circumstances that the breathing muscles are unable to maintain normal oxygen levels in the blood.

When increased WOB requires treatment, therapy may be indicated to increase the blood oxygen level. This is conventionally accomplished in one of two primary ways. The first line of treatment is to increase the oxygen percentage in the inspired air, using supplementary oxygen. If this therapy fails, the next level of treatment is to decrease WOB using positive pressure to assist inspiration. Positive airway pressure (PAP) may be continuous (CPAP) or bi-phasic so that higher pressure is supplied during inspiration than during expiration. PAP is usually applied by blowing oxygen-enriched air into a sealed face mask from a device that regulates the mask pressure by varying the gas flow rate.

Nevertheless, there remains a need for an improved method for reducing the work of breathing.

SUMMARY OF THE INVENTION

The present invention relates to a method for reducing the work of breathing. Heated and humidified air is delivered through a nasal cannula to the is nasal passageway of a patient at a flow rate above 20 liters/min thereby reducing inspiratory work.

BRIEF DESCRIPTION OF THE DRAWINGS

FIG. 1 is a graphical depiction of the pressure-time integral and the inspiratory part of the waveform.

FIG. 2 is a graph of the lowest inspiratory tracheal pressure in centimeters of water against nasal airflow.

FIG. 3 is a graph of the inspiratory work calculated by integrating the inspiratory pressure against time.

FIG. 4 is a graph of the total work plotted against the nasal flow.

FIG. 5 is a typical pressure wave recorded in the pharynx at a nasal flow of zero liters/min.

DETAILED DESCRIPTION OF THE INVENTION

Figure 6:
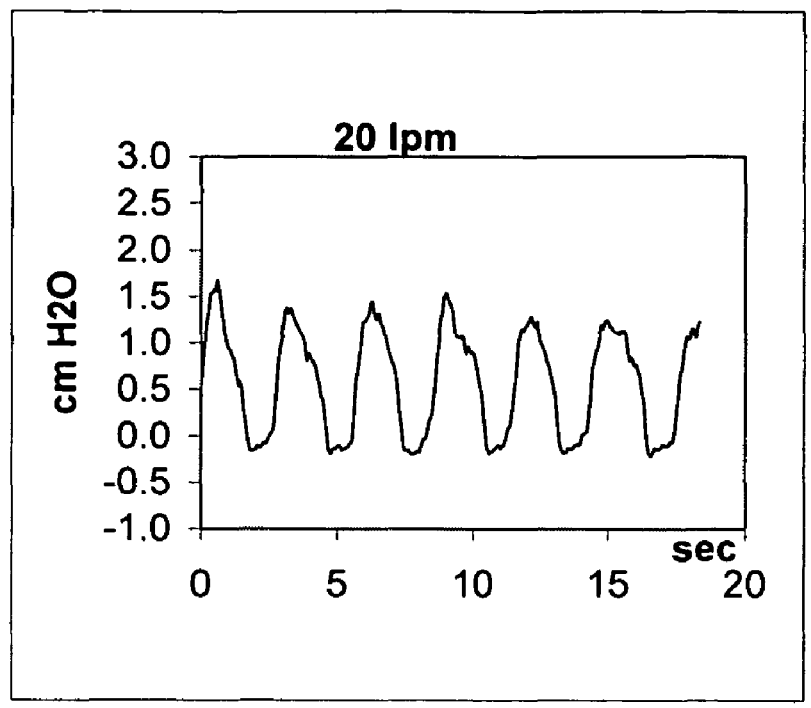
FIG. 6 is a typical pressure wave recorded in the pharynx at a nasal flow of twenty liters/min.

Aspects of this invention will now be described with reference to specific examples and embodiments selected for illustration in the figures. It will be appreciated that the spirit and scope of this invention is not limited to the selected examples and embodiments, and that the scope of this invention is defined separately in the appended claims. It will also be appreciated that the figures are not drawn to any particular proportion or scale, and that many variations can be made to any particular proportion or scale, and that many variations can be made to the illustrated embodiments without departing from the spirit of this invention.

According to an exemplary aspect of this invention, heated and humidified air is delivered to the nasal passageway of a patient via a nasal cannula. Such heated and humidified air can be delivered using an apparatus such as those disclosed in pending application Ser. No. 10/149,356, which is incorporated herein by reference in its entirety.

It has now been discovered that increasing the flow of heated and humidified air into a patient's nasal passageway via a nasal cannula decreases or reduces WOB. It has further been discovered that the preferred flow rate is above 20 liters/min., and that a more preferred flow rate is above about 25 liters/min. As the flow rate increases, it has been discovered that the WOB decreases. However, flow rate exceeding about 40 liters/min can create more pressure and can become uncomfortable for the patient. Furthermore, high humidity cannot be retained easily at a high flow rate above about 40 liters/min.

At flows greater than 20 liters/min, the work normally required to inspire against the resistance of the nose is effectively abolished. A high nasal flow injects air directly into the pharynx, raising the mean pressure. At nasal flows greater than 20 liters/min, inspiratory flow almost never exceeds nasal flow causing pharyngeal pressure to remain at or above atmospheric pressure. Therefore, little or no work is done in inspiring air through a nasal resistance.

WOB can be measured by recording the airway pressure waveform as shown in FIG. 1. Esophageal pressure closely tracks lung pressure so this is also used as a good approximation to the pressure excursions in the lung airways, which are usually less accessible for measurement. Integration of the inspiratory part of the waveform (hatched area in FIG. 1) is then performed electronically. The pressure-time integral is a direct measure of a component of the inspiratory work attributable to the nasal resistance.

EXAMPLE I

The tracheal pressure waveform of a patient was recorded via a tracheal cannula, while the patient received oxygen by nasal cannula at flows from 10 to 35 liters/min. Pressure waveforms were integrated for calculation of WOB. At each nasal flow rate, the average value for ten breaths was calculated. Results are shown in FIG. 2 and FIG. 3.

FIG. 2 shows the lowest inspiratory tracheal pressure in centimeters of water against nasal airflow. As the nasal flow increased, the airway pressure became less negative so that less muscle work was required to create the inspiratory pressure swing.

FIG. 3 shows the inspiratory work calculated by integrating the inspiratory pressure against time. The data show a progressive reduction in inspiratory work at flows above 20 liters/min. The error bars in FIG. 3 highlight the standard error of the mean.

Although high nasal flow produces a modest increase in expiratory work, this is not enough to offset the reduction in inspiratory work. FIG. 4 shows the total work (inspiratory+expiratory) plotted against nasal flow. As for the inspiratory work illustrated in FIG. 3, the total work illustrated in FIG. 4 decreased at nasal flows above 20 liters/min.

EXAMPLE II

Figure 7:
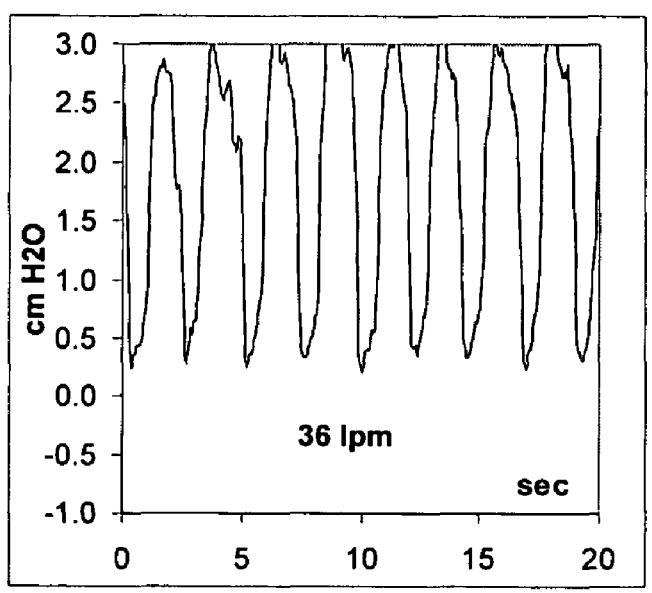
FIG. 7 is a typical pressure wave recorded in the pharynx at a nasal flow of thirty-six liters/min.

In pharyngeal airway pressure tests, subjects were fitted with a cannula for monitoring pressure in the pharyngeal airway. Pressure waveforms were recorded during breathing while warmed and humidified air was administered by nasal cannula. FIG. 5, FIG. 6, and FIG. 7 show typical pressure waves recorded in the pharynx at, respectively, 0, 20, and 36 liters/min nasal flow.

Results show that the average value of the pressure waveform had substantially equal areas above and below zero (atmospheric) pressure at zero flow. But with increasing flow rates, the pharyngeal pressure became increasingly positive. At 36 liters/min, for example, the pharyngeal pressure remained above atmospheric pressure, even during peak inspiration, as illustrated in FIG. 7.

In FIG. 7, the minimum inspiratory pressure reached was about +0.5 cm water, compared with about −0.7 cm in FIG. 5 at 0 liters/min. At 20 liters/min (FIG. 6), the minimum pressure was approximately atmospheric (zero).

These findings indicate that at flows greater than 20 liters/min, the work normally required to inspire against the resistance of the nose is effectively abolished. Though the exact mechanism is not known for certain, it is believed that the high nasal flow injects air directly into the pharynx, thereby raising the mean pressure. During expiration the pharyngeal pressure rises, as air flow from the lungs is added to the nasal flow. During inspiration, air is withdrawn from the pharynx. However, at nasal flows greater than 20 liters/min, the inspiratory flow never exceeds the nasal flow and so the pharyngeal pressure does not fall below atmospheric pressure. Accordingly, at such nasal flows, no work is done in inspiring air through the nasal resistance.

Figure 8:
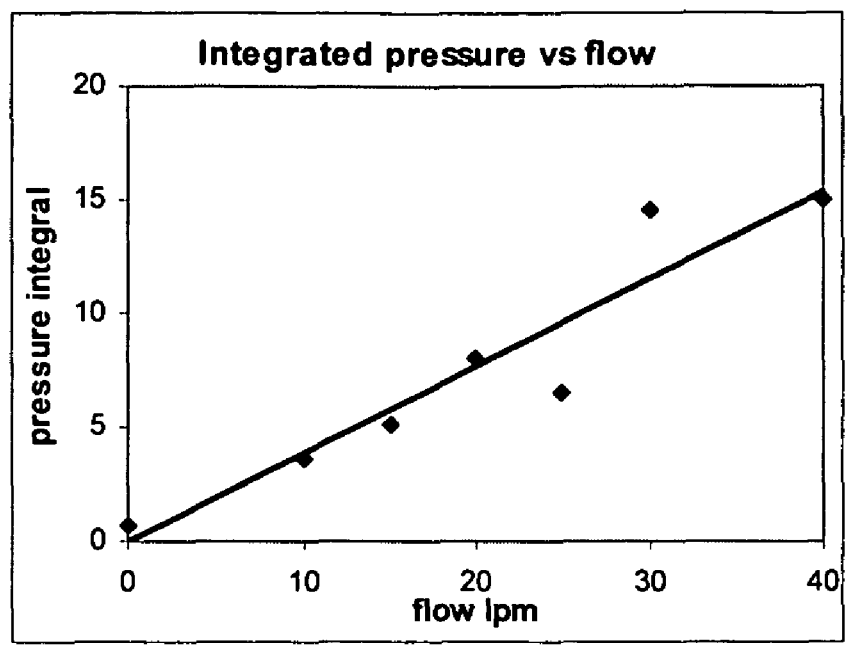
FIG. 8 is a graph of changes in total integrated airway pressure plotted against nasal flow of up to forty liters/min.

FIG. 8 illustrates the changes in total integrated airway pressure (inspiratory plus expiratory) with nasal air flow at flow rates up to forty liters per minute. When the flow is zero, the integral is zero because the inspiratory area is equal to the expiratory area. Thus, the integral becomes increasingly positive as the flow rate increases, illustrating a decrease in inspiratory work.

The observed effects of high nasal flow on pressures in the pharynx and trachea are consistent with a reduction in WOB. Though it was generally considered that reduction in WOB required positive pressure applied during inspiration, it has been discovered that high nasal flows may be beneficial in treating respiratory conditions where work of breathing is elevated, without the complicated and intrusive equipment currently in use for PAP or CPAP.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for reducing the work of breathing comprising:
   generating heated and humidified air in an air generating device; and
   reducing inspiratory work by delivering only the heated and humidified air to a nasal passageway of a patient through a device having a nasal cannula, the delivered heated and humidified air being at least about 95% humidified, the nasal cannula being configured to allow only the heated and humidified air to flow through the nasal cannula at a flow rate above 20 liters/min and below 40 liters/min.

2. The method defined in claim 1, wherein heated and humidified air is delivered to the nasal passageway of the patient at a flow rate above about 25 liters/min.

3. The method defined in claim 1, further comprising maintaining the pharyngeal pressure at or above atmospheric pressure during inspiration.

4. The method defined in claim 1, further comprising delivering the heated and humidified air at about 37° C.

5. The method defined in claim 1, wherein the heated and humidified air is substantially fully saturated.

6. A method for reducing the work of breathing comprising:
   providing a gas flow generating device and a nasal cannula in fluid communication with the gas flow generating device, the nasal cannula configured to allow flow of a gas in only a single direction;
   heating and humidifying a breathing gas in the gas flow generating device;
   passing only the heated and humidified breathing gas from the gas flow generating device to the nasal cannula; and
   reducing inspiratory work by delivering only the heated and humidified breathing gas from the nasal cannula to a nasal passageway of a patient at a flow rate above 20 liters/min and below 40 liters/min and at a relative humidity level of at least about 95%.

7. The method defined in claim 1, wherein the heated and humidified air is delivered without condensation.

8. The method defined in claim 6, wherein the heated and humidified breathing gas is delivered without condensation.

9. The method defined in claim 1, wherein the heated and humidified air has a water vapor content of at least about 40 milligrams per liter and at most about 50 milligrams per liter.

10. The method defined in claim 6, wherein the heated and humidified air has a water vapor content of at least about 40 milligrams per liter and at most about 50 milligrams per liter.

* * * * *